US00PP34180P2

(12) United States Plant Patent
NeSmith

(10) Patent No.: US PP34,180 P2
(45) Date of Patent: May 3, 2022

(54) SOUTHERN HIGHBUSH BLUEBERRY PLANT NAMED 'TH-1996'

(50) Latin Name: *Vaccinium corymbosum*
Varietal Denomination: TH-1996

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/476,112

(22) Filed: Sep. 15, 2021

(51) Int. Cl.
*A01H 5/08* (2018.01)

(52) U.S. Cl.
USPC ..... Plt./157

(58) Field of Classification Search
USPC ..... Plt./157
See application file for complete search history.

*Primary Examiner* — Susan McCormick Ewoldt
(74) *Attorney, Agent, or Firm* — Thomas Horstemeyer, LLP

(57) ABSTRACT

A new and distinct cultivar of *Vaccinium* plant named 'TH-1996', characterized by a combination of early season ripening; large berries with good scar and flavor; moderately vigorous growth; and a low chilling requirement of about 100 hours, or less, below about 45° F.

5 Drawing Sheets

Botanical designation: *Vaccinium corymbosum.*
Cultivar denomination 'TH-1996'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-1996'.

The new *Vaccinium corymbosum* 'TH-1996' was first identified in 2013 in Griffin, Ga. The new variety 'TH-1996' is early season, ripening after the early commercial varieties 'TH-819' Georgia Dawn™ (U.S. Plant Pat. No. 24,696) in south Georgia but before 'Rebel' (U.S. Plant Pat. No. 18,138) and more vigorous than 'Rebel'. 'TH-1996' has large, firm berries with a good scar, and a very low chilling requirement of about 100 hours or less below 45° F. when produced under typical low to mid chill production areas in temperate regions. Preliminary trials of 'TH-1996' in "no-chill' regions of low latitude in Peru indicated it also performs well as an evergreen or ever-bearing variety and has the potential to adapt to conditions in such regions.

'TH-1996' originated from seeds collected from open-pollination of 'Snowchaser' (U.S. Plant Pat. No. 19,503). The open-pollinated fruit of 'Snowchaser' were first harvested from trial plots in 2010 by D. Scott NeSmith. The new blueberry plant variety 'TH-1996' has been tested in asexually propagated (by vegetative cuttings) plantings in Alapaha, Ga. since 2014 where it was established for testing and comparing to industry standards. 'TH-1996' was also entered into preliminary trials and observation in Peru in 2017. Observations of the resulting 'TH-1996' progeny have shown that the unique features of this new *Vaccinium corymbosum* 'TH-1996' are stable and reproduced true to type in successive generations.

SUMMARY OF THE INVENTION

The new *Vaccinium* cultivar 'TH-1996' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-1996'. In combination, these traits set 'TH-1996' apart from all other existing varieties of southern highbush blueberry known to the inventors:

1. early season, ripening later than early variety Georgia Dawn™ and before 'Rebel' in south Georgia;
2. produces berries that are larger and firmer than Georgia Dawn™, larger than maternal parent 'Snowchaser', and with better flavor as compared to 'Rebel';
3. moderately vigorous growth that is more vigorous than 'Rebel' and Georgia Dawn™;
4. very low chilling requirement of about 100 hours or less below about 45° F. (based on comparison of flowering dates with those of known standard cultivars) when produced under typical low to mid chill production areas in temperate regions;

Comparison: As compared to the female parent 'Snowchaser', plants of *Vaccinium* 'TH-1996' have larger berry size, a drier picking scar, and lower chill requirement.

Plants of the new *Vaccinium* can also be compared to commercial early season southern highbush blueberry cultivars 'Rebel' (U.S. Plant Pat. No. 18,138) and 'TH-819' Georgia Dawn™ (U.S. Plant Pat. No. 24,696). The new variety is early season and begins ripening after the early variety Georgia Dawn™ in south Georgia, but before Rebel. 'TH-1996' has berries that are larger and firmer than 'Georgia Dawn' at Alapaha (Table 1). When compared to 'Rebel', fruit of 'TH-1996' has better flavor and the plant is more vigorous (Table 1). No notable diseases or other pest problems have been observed for the new variety that are not also common for other varieties. The new variety is estimated to have a chilling requirement of about 100 hours, or less, below about 45° F. (based on comparison of flowering dates with those of known standard cultivars) when produced under typical low to mid chill production regions. Additional comparison data of 'TH-1996' with Georgia Dawn™ and 'Rebel' are presented in the tables below.

Due to the very low chill requirement, the new *Vaccinium* 'TH-1996' flowers very early and requires frost protection for successful production in temperate regions. Preliminary trials of 'TH-1996' in "no-chill" regions of low latitude in Peru have indicated it performs well as an evergreen or ever-bearing variety. Finding varieties that produce well in such regions is a challenge, and observations have revealed that 'TH-1996' appears to have the potential to adapt to such conditions.

TABLE 1

3-year average ratings (2019-2021) of some fruit and plant characteristics of blueberry 'TH-1996' and comparison cultivars Georgia Dawn ™ and 'Rebel' in field test plots at Alapaha, Ga. Rating scales are based on a 1 to 10 score, with 1 being the least desirable and 10 being the most desirable. Plants were established 2017.

| | Georgia Dawn ™ | 'Rebel' | 'TH-1996' |
|---|---|---|---|
| Berry size | 6.9 | 7.5 | 7.5 |
| Berry scar | 7.0 | 7.2 | 7.2 |
| Berry color | 7.0 | 7.2 | 7.2 |
| Berry firmness | 6.8 | 7.2 | 7.0 |
| Berry flavor | 7.2 | 6.0 | 7.0 |
| Cropping | 5.0 | 7.0 | 4.5 |
| Plant vigor | 8.0 | 7.8 | 8.5 |
| Date of 50% flowering | Feb. 9 | Feb. 15 | Feb. 3 |
| Date of 50% ripening | Apr. 20 | Apr. 25 | Apr. 23 |
| Fruit development period (days) | 69 | 69 | 79 |

BRIEF DESCRIPTION OF THE DRAWINGS

The accompanying colored photographic illustrations show the overall appearance and distinct characteristics of the new cultivar of *Vaccinium corymbosum* 'TH-1996' showing the colors as true as possible. Colors in the photographs may differ slightly from the color values cited in the detailed botanical description, which accurately describes the colors of the new *Vaccinium corymbosum* 'TH-1996'. Photographs were taken of plants grown outdoors in Alapaha, Ga. during different years.

The photograph labeled

Figure 1:
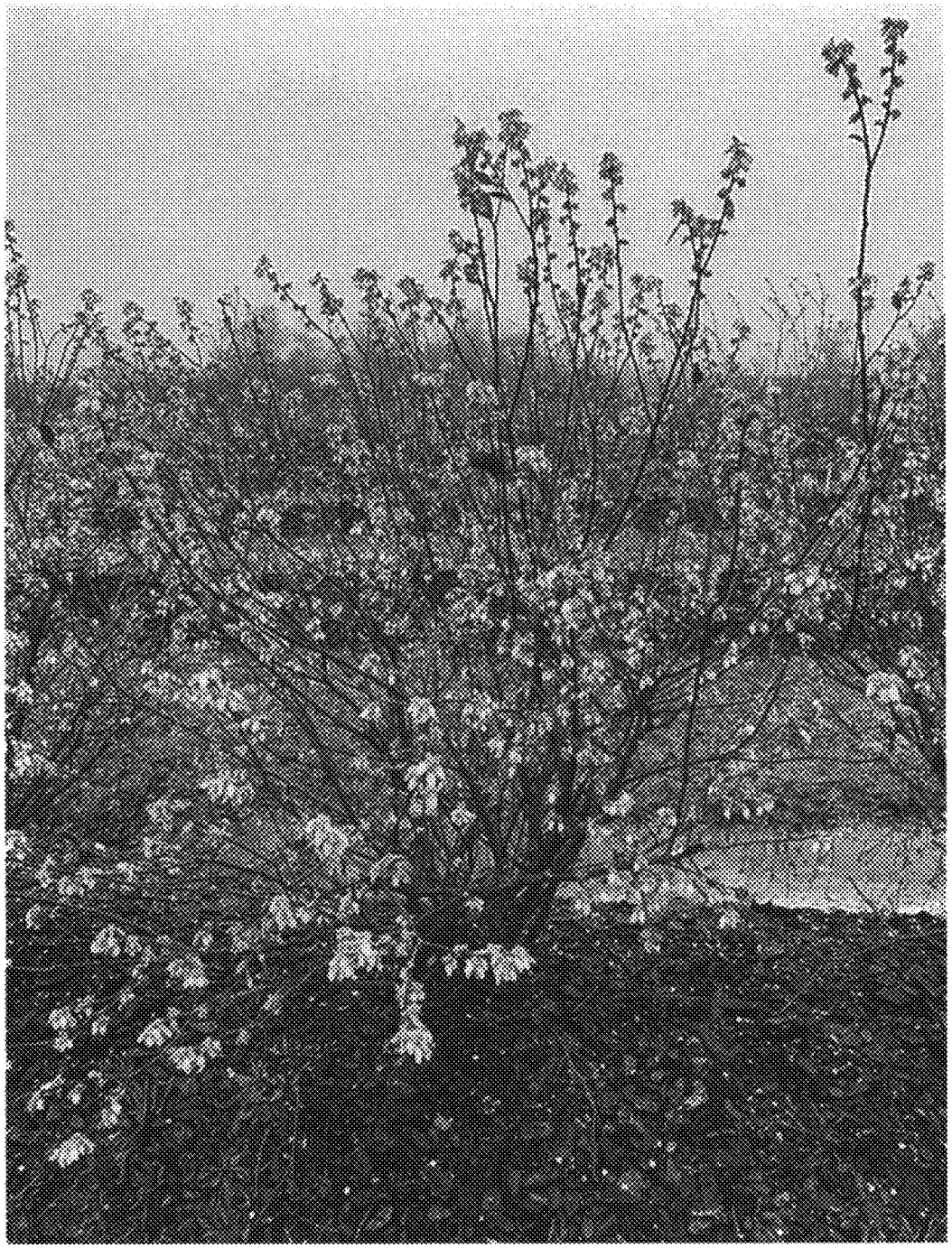
FIG. 1 depicts 4-year old plants of 'TH-1996' showing flowers and overall form of the plant. Photographs were taken in February 2021.
Figure 2:
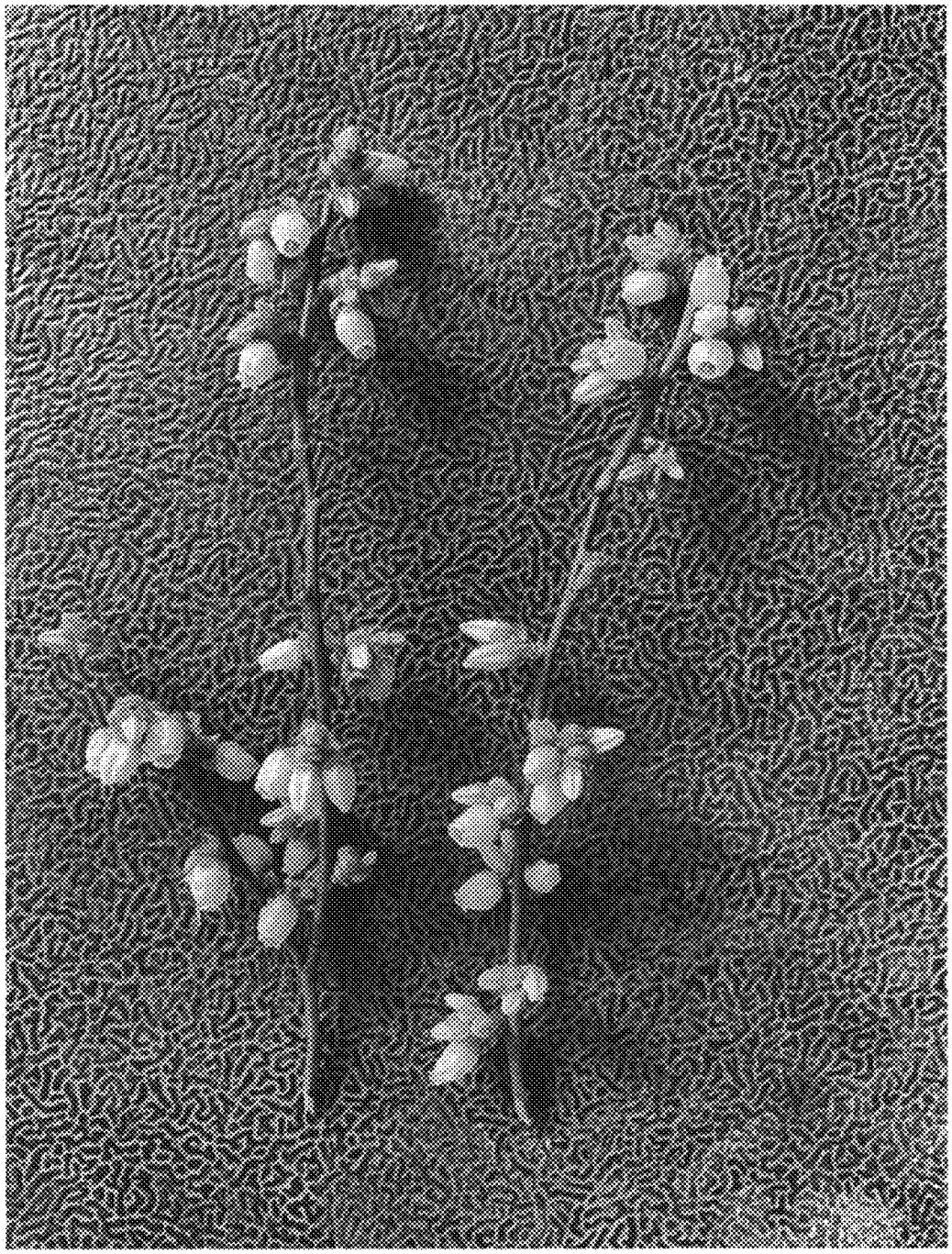

The photograph labeled FIG. 2 was taken in February 2021 and shows a close-up of flowering branches of 'TH-1996'.

Figure 3:
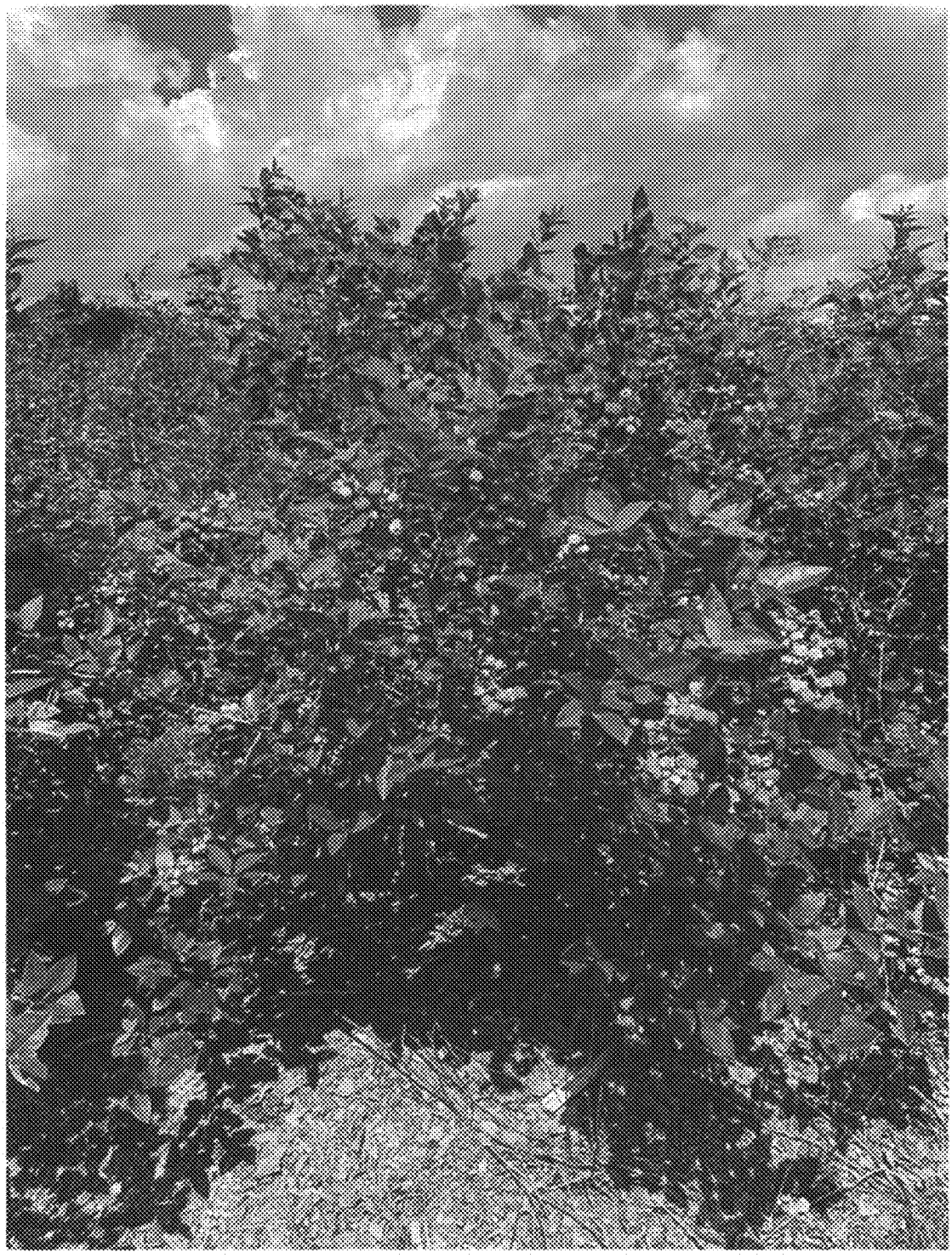

The photograph labeled FIG. 3 depicts mature 4-year old 'TH-1996' plants during fruit ripening showing large berries. Photographs were taken in May 2021.

Figure 4:
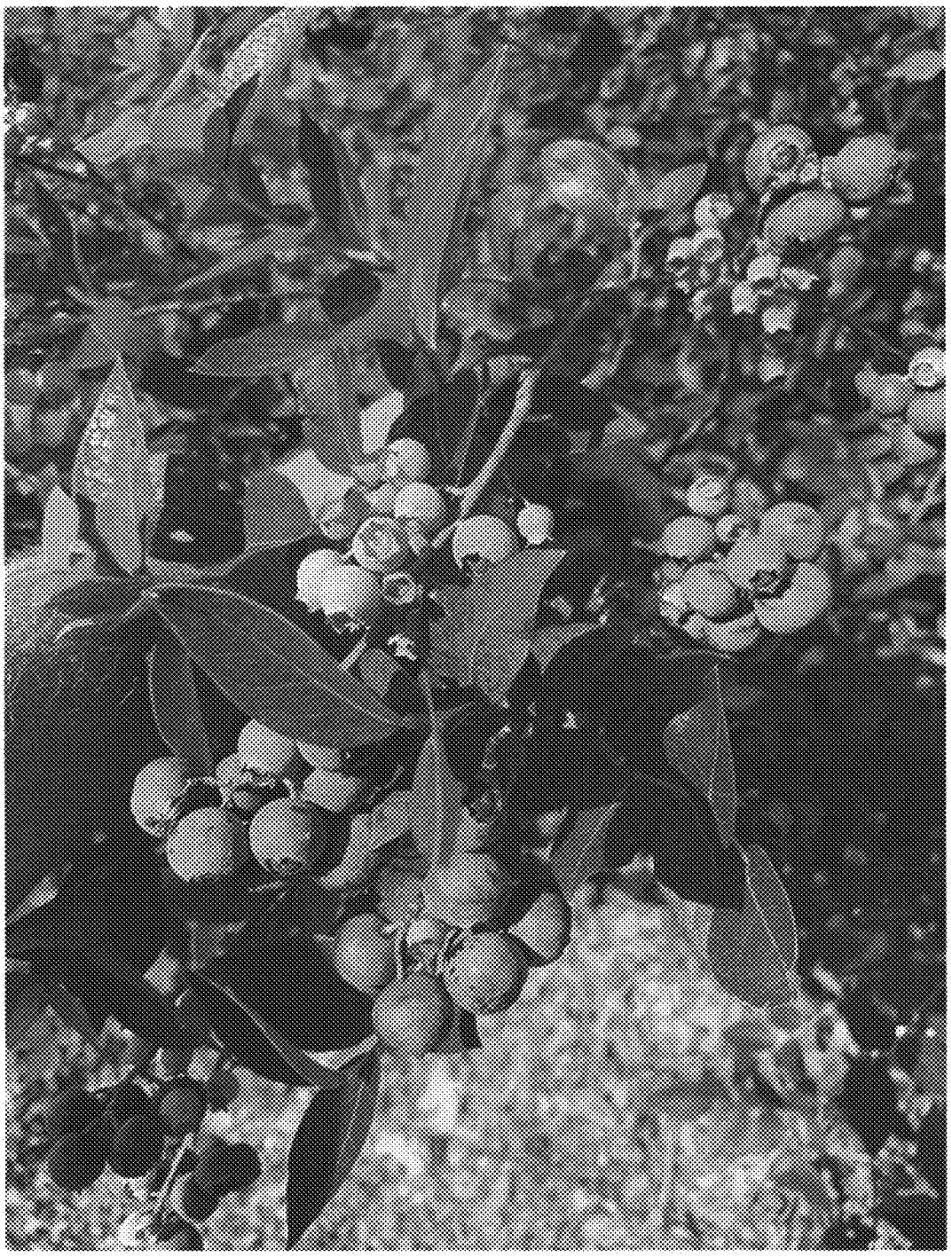

The photograph labeled FIG. 4 depicts a close-up view of a branch of a typical 4-year old 'TH-1996' plant during fruit ripening showing the large berry size and good color taken in May 2021.

Figure 5A:
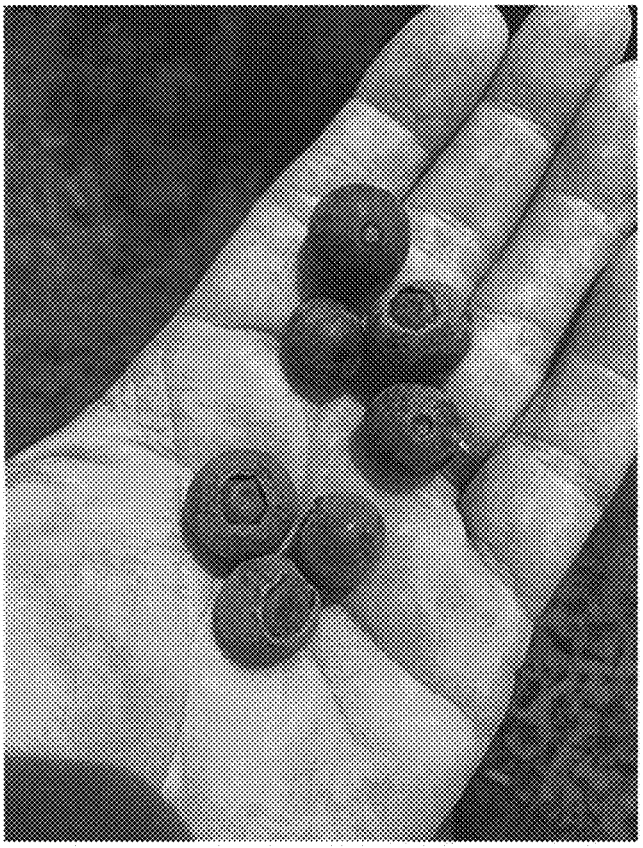
Figure 5B:
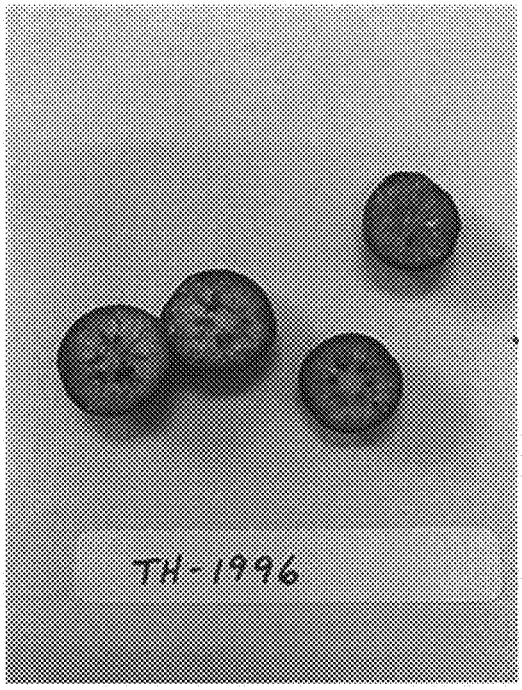

The photographs labeled FIGS. 5A-5B depict close-up views of fruit of 'TH-1996'. FIG. 5A is a close-up view of ripe fruit of 'TH-1996' in a human hand, and FIG. 5B shows a cross sectional view of the interior of the fruit.

DETAILED BOTANICAL DESCRIPTION

The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TH-1996'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-1996'. Where dimensions, sizes, colors, and other characteristics are given, it is to be understood that such characteristics are approximations and averages set forth as accurately as practicable. Data were collected between the years of 2017-2021 from horticulture farms and nurseries in Alapaha, Ga. from 3 to 4-year-old plants (planted in the field with supplemental irrigation). The average low temperature for the year ranges from about 54° F. to 58° F., and the average high temperature for the year ranges from about 78° F. to 82° F.

Botanical classification: *Vaccinium corymbosum* 'TH-1996'.

*Commercial classification.*—Fruit-bearing shrub.

*Parentage.*—Open pollination of *Vaccinium corymbosum* 'Snowchaser' (U.S. Plant Pat. No. 19,503).

Growth and propagation:

*Propagation type.*—Vegetative by softwood cuttings.

*Growth rate.*—Moderately vigorous.

*Root description.*—Fibrous.

Plant description:

*Growth habit.*—Plant is dense with mostly spreading habit, typically having about 1 to 3 main canes arising from the crown, with multiple branching of shoots within about 10 cm of the soil surface from those canes. Main canes can fuse together forming a pseudo single main cane 30 to 60 mm in diameter.

*Usage.*—Commercial fruit production primarily.

*Productivity.*—Medium to high crop/yield with yields of about 6 to 9 lbs per plant possible on plants 4-years-old or older grown under well-fertilized and irrigated field conditions with frost protection.

*Size of plant.*—Plant is about 1.3 to 1.5 m tall by about 4 years. The plant crown, or base, is narrow, typically about 10 to 20 cm in diameter. Upper portion of plant canopy reaches about 1.3 to 1.6 m in diameter by about 4 years.

*Cold hardiness.*—Similar to southern highbush varieties such as 'TH-819' Georgia Dawn™ (U.S. Plant Pat. No. 24,696) and 'Rebel' (U.S. Plant Pat. No. 18,138).

*Disease resistance.*—No exceptional disease resistance or susceptibility observed. Typical for southern highbush such as Georgia Dawn™ and 'Rebel'.

*Chilling requirement.*—Plants are very low chill, requiring only about 100 hours, or less, of temperatures at or below about 7° C. to induce normal leafing and flowering during the spring under conventional dormant production systems. 'TH-1996' has also shown a strong propensity for evergreen production with no chilling when grown under lower latitude locations such as Peru. The chill requirement is lower than the female parent 'Snowchaser'.

*Leafing.*—Plants tend to break sufficient leaf buds simultaneously with, or shortly after, anthesis.

*Canes.*—Main cane base diameter about 20 to 35 mm, color most near Brown N200C to Grey 201C; two-year-old cane diameter about 10 to 15 mm, color transitioning from Yellow Green 145B to Greyed Orange 166A; current season wood diameter about 3 to 8 mm, color Yellow Green 145B.

*Fruiting wood.*—Moderate number of twigs of about 10 to 15 cm in length, with internode lengths of about 15 to 25 mm common.

Foliage:

*Leaf color.*—Healthy mature leaves: top side of leaf color is Green N137B, under side of leaf color is Yellow Green 138B.

*Leaf arrangement.*—Alternate, simple.

*Leaf shape.*—Elliptic.

*Leaf margins.*—Nearly entire, some slight serration occasionally observed.

*Leaf venation.*—Pinnate with slight netting.

*Leaf apices.*—Broadly acuminate.

*Leaf bases.*—Acute.

*Leaf dimensions.*—Length: about 50 to 65 mm; width: about 25 to 35 mm.

*Petioles.*—Small, about 3.0 to 4.0 mm long, about 1.8 to 2.3 mm wide; Color: Yellow Green 145C.

*Texture.*—Leaf margins, nearly smooth; both upper and lower leaf surfaces, glaucous.

Flowers:

*Date of* 50% *anthesis.*—3-year average January 25 to February 5 in southeast Georgia.

*Flower shape.*—Urceolate.

*Flower bud number.*—Very high, averaging 5 to 10 buds per fruiting shoot.

*Flowers per cluster.*—5 to 7 common.

*Flower fragrance.*—None detected.

*Corolla color.*—White N155D to White NN155C once fully expanded (open); Red Purple 62C can often be observed in early stages of corolla expansion, especially in cool springs.

*Corolla length.*—About 7.5 to 8.5 mm.

*Corolla width.*—About 5.0 to 6.0 mm.

*Corolla aperture width.*—About 2.5 to 4.0 mm.

*Flower peduncle.*—Length about 4.0 to 9.0 mm; Color: Green 138D.

*Flower pedicel.*—Length about 3.0 to 4.0 mm; Color: Green 138D.

*Calyx* (*with sepals*).—Diameter: about 5.0 to 6.5 mm; Color: sepals Green 138D; calyx center Green 138B to 138C.

*Stamen.*—Length: about 6.0 to 7.0 mm; number per flower: about 10; filament color: Green White 157D.

*Style.*—Length: about 7.5 to 8.5 mm; Color: Yellow Green 145B.

*Pistil.*—Length: about 9.5 to 10.5 mm; ovary color: Green 138D.

*Anther.*—Length: about 3.5 to 4.5 mm; number: 10; Color: Greyed Orange 164A to 164B.

*Pollen.*—Abundance: high; Color: Yellow White 158A.

*Compatibility.*—The cultivar has a small to moderate degree of self-compatibility.

Fruit:

*Date of* 50% *maturity.*—3-year average April 20 to 27 in southeast Georgia.

*Fruit development period.*—About 78 to 84 days.

*Berry color.*—With wax Blue 100C; with wax removed Black 203C.

*Berry flesh color.*—Green White 157D.

*Berry surface wax abundance.*—Medium to high.

*Berry weight.*—$1^{st}$ harvest: about 2.5 to 3.0 g; $2^{nd}$ harvest: about 2.2 to 2.6 g.

*Berry size.*—Height from calyx to scar: about 14 to 16 mm; diameter: about 18 to 20 mm.

*Berry shape.*—Semi-spherical.

*Fruit stem scar.*—Medium to large, dry, with occasional hearing upon harvest.

*Calyx.*—Depth shallow, nearly flat, less than about 1.0 mm; width, about 6.0 to 9.0 mm; sepals typically not visible, slightly turned inward and flat when present.

*Berry firmness.*—Fair to good firmness.

*Berry flavor and texture.*—Very smooth texture, mildly sweet, low acidity; can be bland if over-ripe.

*Storage quality.*—Fair to good.

*Suitability for mechanical harvesting.*—Not suitable.

*Uses.*—Primarily intended for fresh fruit for shipping and processing markets.

Seed:

*Seed abundance in fruit.*—Medium, about 10-15 fully developed seeds/berry.

*Seed color.*—Greyed Orange 166C.

*Seed dry weight.*—About 35-45 mg per 100 seed.

*Seed size.*—About 1.2 to 1.8 mm long.

It is claimed:

1. A new and distinct cultivar of the *Vaccinium* plant named 'TH-1996' as illustrated and described herein.

* * * * *